United States Patent [19]

Striebel, II et al.

[11] Patent Number: 5,316,013
[45] Date of Patent: May 31, 1994

[54] ORIENTED BIOPSY NEEDLE ASSEMBLY

[75] Inventors: Robert L. Striebel, II, Wyoming; Kenneth E. Chettleburgh, Sparta; Alan N. Taylor, Rockford, all of Mich.

[73] Assignee: Hart Enterprises, Inc., Wyoming, Mich.

[21] Appl. No.: 749,523

[22] Filed: Aug. 26, 1991

[51] Int. Cl.$^5$ .............................................. A61B 10/00
[52] U.S. Cl. ................................. 128/754; 606/171; 24/616
[58] Field of Search ............... 128/754, 753, 752, 751, 128/750, 749; 606/167, 170, 171, 172, 184, 185; 604/164, 165, 166; 24/616, 614, 615

[56] References Cited

U.S. PATENT DOCUMENTS

| 306,070 | 2/1990 | Akerfeldt | D24/25 |
|---|---|---|---|
| 309,014 | 7/1990 | Akerfeldt | D24/25 |
| 3,430,306 | 3/1969 | Tareau | 24/615 |
| 3,477,423 | 11/1969 | Griffith | 128/754 |
| 4,266,555 | 5/1981 | Jamshidi | 128/753 |
| 4,559,679 | 12/1985 | Downey | 24/615 |
| 4,600,014 | 7/1986 | Beraha | 128/754 |
| 4,609,370 | 9/1986 | Morrison | 604/165 |
| 4,699,154 | 10/1987 | Lindgren | 128/754 |
| 4,735,215 | 4/1988 | Goto et al. | 128/754 |
| 4,881,551 | 11/1989 | Taylor | 128/754 |
| 4,944,308 | 7/1990 | Akerfeldt | 128/751 |
| 5,027,481 | 7/1991 | Frano | 24/606 |
| 5,031,634 | 7/1991 | Simon | 128/754 |
| 5,036,860 | 8/1991 | Leigh et al. | 128/754 |

Primary Examiner—Stephen C. Pellegrino
Assistant Examiner—Guy V. Tucker
Attorney, Agent, or Firm—Waters & Morse

[57] ABSTRACT

The oriented biopsy needle assembly includes a cannula hub assembly having a cannula hub fixedly attached to the proximal end of a cannula and a barrel member integral with the proximal end of the cannula hub. The barrel member and cannula hub have longitudinally coaxial bore therethrough axially aligned with and extending to the cannula. A pair of inwardly flexible finger pinching arms formed integral with and extending lengthwise over the outer surface of the barrel member are aligned opposite to each other, and each arm has an inwardly extending detent positioned to be downwardly flexed into oppositely aligned corresponding cutout slots of the barrel member. The cannula hub assembly cooperates with a stylet hub at a proximal end, a shoulder portion at a distal end of the hub, and a distal stem portion extending distally from the shoulder portion and terminating at a distal end fixedly attached to the proximal end of a sampling stylet. This distal end includes a tip member which cooperates with the walls defining the longitudinal coaxial bore of the barrel member to allow the distal end and tip member to be slidably received into the bore only when the tip member is oriented such that the sharpened distal ends of the cannula and sampling stylet are oppositely directed, and further includes a pair of oppositely aligned bi-directionally, flexible latching flanges which are received into the cutout slots of the barrel member to thereby orientate the stylet hub in a proximally retracted removably latched spaced relationship to the cannula hub. An inward flexing of the flexible finger pinching arms extends the inwardly extending detents into the cutout slots to co-act with and inwardly flex the pair of flexible latching flanges to thereby allow proximal withdrawal of the sampling stylet from the cannula so that multiple biopsies may be obtained with one insertion of the cannula.

6 Claims, 4 Drawing Sheets

ORIENTED BIOPSY NEEDLE ASSEMBLY

BACKGROUND OF THE INVENTION

1. Field of the Invention

The present invention relates to a disposable soft tissue biopsy instrument or more specifically, a cannula and stylet needle assembly. The disposable biopsy instrument of the present invention provides an oriented, spaced relationship between a hub of an inner sampling stylet and a hub of an outer cannula. The assembly is oriented such that the sharpened distal ends of the cannula and of the sampling stylet are oppositely directed and cannula and stylet hub subassemblies of the needle assembly allow for quick proximal withdraw of the sampling stylet from the cannula for inspection of the sample without removal of the cannula from the biopsy site.

More specifically, the stylet and cannula hub subassemblies are constructed: (a) to provide for smooth forward advance of the stylet hub assembly into the cannula hub assembly with minimal force forwardly when an actuating device causes relative movement between the subassemblies: (b) with flexing flanges on the stylet hub assembly and mating slots in a barrel of the cannula hub assembly which engage each other for positioning the cannula needle and stylet in a desired firing position and which prevent accidental backout of the stylet hub assembly from the cannula hub assembly; (c) to provide the flexing flanges with flexibility forwardly, rearwardly and laterally so that the flanges can absorb stress imposed thereon during forward overtravel of the cannula relative to the stylet when the actuating device is fired; and, (d) with pincher arms each having a radially inwardly facing detent which can be pushed into one of the slots to unlatch the stylet hub assembly from the cannula hub assembly to permit removal of the stylet without removing the cannula.

2. Description of the Related Art including information Disclosed Under 37 CFR 1.97–1.99

Sampling of inner tissue on humans and animals, a so-called biopsy, has become an increasingly common procedure for the diagnosis of malignancies and for other medical uses. Typically, biopsy instruments include a needle assembly comprising a hollow outer needle (cannula) and an inner needle (sampling stylet) slideably positioned therein. The sampling stylet has a sharpened distal end and an adjacent biopsy sample-receiving notch which is telescopically disposed within the cannula and extendible from the distal end of the cannula. When so extended, the surrounding tissue expands into the sample-receiving notch of the sampling stylet. Thereafter the cannula is pushed forward to cover the stylet, thus cutting-out a tissue sample which is thereby collected in the sample-receiving notch of the sampling stylet and retained by the surrounding outer cannula When the tissue sample is taken, typically the entire needle assembly containing the collected tissue sample is withdrawn, whereupon the sample can be taken out and analyzed.

The Travenol TRU-CUTÛ biopsy needle available from Travenol Laboratories, Inc. of Deerfield, Ill. and the subject of U.S. Pat. No. 3,477,423 is an often used biopsy needle comprising a hollow tubular cutting cannula having a sharpened distal end attached to a plastic handle. A coaxial solid stylet telescopes within the cannula and is attached to a knob at its proximal end. The distal end of the stylet is sharpened and includes a traverse slot or specimen notch adjacent to the sharpened end. To obtain a biopsy sample using the Travenol needle, the physician positions the stylet up to or in front of the area to be biopsied, whereupon advancement of the needle assembly is halted. The stylet is then manually advanced distally of the cannula with the cannula held stationary. Upon advancement of the stylet, the specimen notch is exposed. Tissue surrounding the stylet contracts into the specimen notch and the cutting cannula is then manually advanced distally over the stylet, slowly shearing off the tissue entrapped in the stylet's specimen notch. The instrument is then withdrawn and the stylet advanced distally to expose the tissue for preparation for study. If the sampling was not successful, the stylet may be reinserted into the cannula, which remains positioned within the patient, and an attempt can be made to reposition the assembly of the stylet and the cannula to repeat sampling.

Such technique using this basic design of a biopsy instrument is referred to as a manual technique. One drawback to the manual technique is that it requires a great deal of manual dexterity and motor coordination, along with the use of both hands, to advance the stylet while maintaining the position of the cannula and then to maintain the position of the stylet while advancing the cannula.

The Beraha U.S. Pat. No. 4,600,014 discloses a transrectal prostate biopsy device which comprises a handle held in a physician's palm, and a guide tube extending forwardly of the handle. A cannula is slidably disposed within the guide tube and is movable from within the guide tube forwardly out of the distal end of the guide tube. A sampling stylet is telescopically disposed within the cannula and projects from the rear of the handle. A knob is provided at the proximal end of the stylet for extending a distal end of the stylet out of the distal end of the guide tube to expose a sampling thereon. The physician holds the handle in one hand using his index finger at the distal end of the guide tube to guide the instrument to a selected transrectal point on the prostate. Upon locating the point, one hand holds the instrument steady while the other hand pushes the stylet forward and then pushes the cannula over the stylet to sever the tissue within the sampling slot. The device is then withdrawn to gain access to the sample. In one embodiment of the device, the cannula, when in the retracted position, is spring loaded by means of a compressed spring. A release lever, which works against the compressed spring can be activated to release compression of the spring which then expands and pushes the cannula outwardly over the stylet.

A fully automatic instrument is described in the Lindgren U.S. Pat. No. 4,699,154. This instrument comprises a reusable, spring-loaded box-shaped housing or handpiece, which activates a disposable cannula and stylet set. Both the stylet and cannula are activated in rapid succession.

The instrument has the advantage of eliminating the dexterity and motor coordination necessary in use of manual device and also eliminates the slow cutting action of the manually advanced cannula and replaces it with a very quick, clean cut.

The Goto et al U.S. Pat. No. 4,735,215 discloses a Soft Tissue Biopsy Instrument wherein a stylet extends through a cannula mounted in a distal outer barrel member and is press-fitted into a stylet hub that is press-fitted into a locking ring that is threadably received on a mounting ring fixed in a proximal outer barrel member. The stylet hub is received in an inner proximal barrel member. To remove the stylet the proximal outer barrel member must be unthreaded from the distal outer barrel member and then the locking ring/stylet hub must be unthreaded from the mounting ring.

In the Taylor U.S. Pat. No. 4,881,551 there is disclosed a soft tissue core biopsy instrument wherein a stylet extends through a proximal outer barrel member and a distal inner barrel member, a proximal portion of which is received in the proximal outer barrel member and through a cannula mounted to a cannula hub received in the distal inner barrel member. A proximal end of the stylet is mounted to a stylet hub which has a bifurcated proximal end portion defined by two fingers. Each finger has a detent thereon which is snap-fittingly received in a recess inside a proximal end of the proximal outer barrel member. The fingers are squeezed together to release the detents from the recesses to remove the stylet. The mating recesses and detents serve to locate the stylet longitudinally and rotationally.

The oriented biopsy needle assembly of the present invention maintains the inner stylet hub and the outer cannula hub in a spaced oriented relationship whereby the user thereof may properly load or position the entire needle assembly into a reusable gun introduced without orientating the stylet hub and cannula hub into the gun individually. Alternatively, the orientation of the stylet hub and cannula hub can be maintained such that the needle assembly can be positioned into the patient without necessarily, or first, loading the needle assembly into a reusable gun. This advantageously allows a physician to pre-position the needle assembly in a patient and scan the area to be biopsied confirming the correct position of the needle with scanner techniques such as MRI, CAT, and ultrasound independent of the reusable gun which is large and heavy and requires the user to maintain control of the gun handpiece at all times. Thereafter the stylet and cannula can be either advanced manually or with the aid of the automatic gun, such as the Radiplast AB tissue sampling device described in the Lindgren U.S. Pat. No. 4,699,154. The oriented spaced relationship between the cannula hub assembly and the stylet hub assembly conforms to the loading position of the Radiplast tissue sampling device merely by establishing a conforming length between the stylet hub and the cannula hub of the needle assembly of the present invention.

Further, the needle assembly of the present invention orients the assembly such that the sharpened distal ends of the stylet and cannula are oppositely directed and are maintained free of undesirable rotation which could hinder successful biopsy collection.

Additionally, the stylet hub assembly is provided with flexing flanges and the cannula hub assembly is provided with mating slots in a barrel of the cannula hub assembly which flanges and slots engage each other for positioning the cannula needle and stylet in a desired firing position and which prevent accidental backout of the stylet hub assembly from the cannula hub assembly by reason of the flexing flanges engaging in the slots; and the flanges being flexible forwardly, rearwardly and laterally so that the flanges can absorb stress imposed thereon during forward overtravel of the cannula relative to the stylet when the actuating device is fired.

Still further, the stylet is proximally removed easily from within the cannula such that examination of the biopsy sample may be taken without removing the cannula from the biopsy site by providing pincher arms on the cannula hub assembly each having a radially inwardly facing detent which can be pushed into one of the slots to unlatch the stylet hub assembly from the cannula hub assembly to permit removal of the stylet without removing the cannula.

The above attendant advantageous features also promote the desirable goals of minimizing the time required for biopsy and providing a disposable surgical instrument adapted for biopsy procedure utilizing scanning technologies.

SUMMARY OF THE INVENTION

According to the invention there is provided an oriented biopsy needle assembly comprising:

a cannula hub assembly including a cannula hub having a proximal end and a distal end and a cannula extending distally from the cannula hub and having a sharpened distal end;

a sampling stylet having a proximal end, a sharpened distal end and a biopsy sample receiving notch adjacent the distal end and being telescopically disposed within the cannula and extendible from the distal end of the cannula;

the cannula hub assembly further including a barrel member fixed to the proximal end of the cannula hub, the barrel member and the cannula hub having a longitudinal coaxial bore therethrough axially aligned with and extending to the cannula;

a stylet hub assembly having a proximal end, a stylet hub at said proximal end, a shoulder portion at a distal end of the hub, and a stem portion extending distally from the shoulder portion and terminating at the distal end of the hub assembly which is fixedly attached to the proximal end of the sampling stylet;

first cooperating means on the cannula hub assembly and the stylet hub assembly for orienting the needle assembly such that the sharpened distal end of the cannula and of the sampling stylet are oppositely directed;

second cooperating means on the cannula hub assembly and the stylet hub assembly for removably latching the stylet distal end within the cannula hub assembly to orientate the stylet hub in a proximately retracted spaced relationship to the cannula hub; and third cooperating means on the cannula hub assembly and the stylet hub assembly for unlatching the stylet distal end from the cannula hub assembly to enable proximal withdrawal of the sampling stylet from the cannula so that multiple biopsies may be obtained with one insertion of the cannula.

DESCRIPTION OF THE PREFERRED EMBODIMENT(S)

Figures 1A, 3, 4A, 4B:
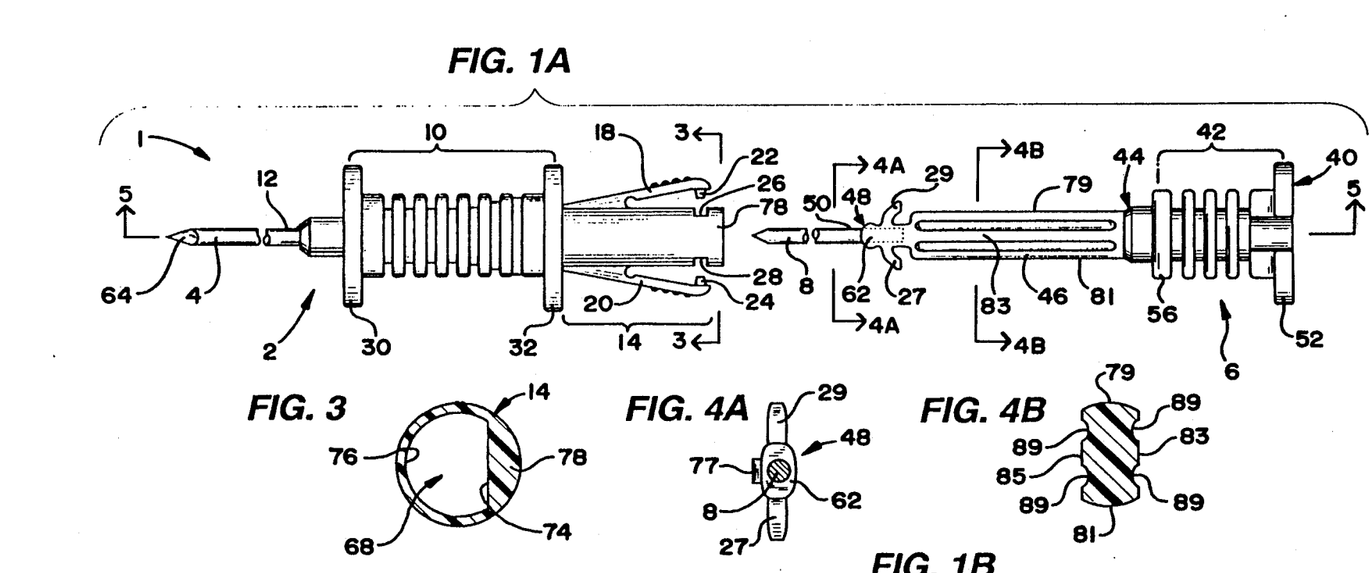
FIG. 1A is a longitudinal top plan view of the oriented biopsy needle assembly of the present invention and shows a cannula hub assembly separated from a stylet hub assembly of the needle assembly.
FIG. 3 is a cross-sectional view through the distal end of the cannula hub assembly and is taken along line 3—3 of FIG. 1A.
FIG. 4A is a front elevational view of the distal end of the stylet hub assembly and is taken along line 4A—4A of FIG. 1A.
FIG. 4B is cross-sectional view through a stem portion of the stylet hub assembly and is taken along line 4—4 of FIG. 1A.

Referring now to the drawings, and more particularly to FIG. 1A, there is shown a top plan view of an oriented biopsy needle assembly 1 of the present invention and its two major components namely, a cannula hub assembly 2 including a cannula 4 and a stylet hub assembly 6 including a sampling stylet 8. The cannula hub assembly 2 includes a cannula hub 10 fixedly attached to a proximal end 12 of the cannula 4 and a barrel member 14 integral with and extending rearwardly from the proximal end 16 of the cannula hub 10. The barrel member 14 has a longitudinal bore or cavity 15 therethrough axially aligned with and extending to the cannula 4. The barrel member 14 further has a pair of inwardly flexible finger pinching arms 18 and 20 aligned opposite each other and formed integrally with the barrel member 14 and extending rearwardly lengthwise from, radially outwardly from, and over the outer surface of barrel member 14.

Each finger arm 18, 20 has an inwardly extending detent, 22 or 24. The detents 22, 24 are inwardly flexed by a pinching of the finger pinching arms 18, 20 to extend them downwardly into corresponding opposing cutout slots 26 and 28 extending through the thickness of the barrel member 14 to co-act with and inwardly move flexible latching flanges 27 and 29 on the stylet hub assembly 6 for unlatching a distal end 48 of the stylet hub assembly 6 received within the cannula hub assembly 2.

The external surface of the cannula hub 10 may comprise a number of diverse designs. For example, as illustrated at FIGS. 1A and 1B, the cannula hub 10 may include a transverse distal flange 30 and transverse proximal flange 32 at the distal and proximal ends, respectively, of the canula hub 10 and may further be ribbed between such transverse flanges with cannula hub rib extensions 33, 34, 35, 36, 37, and 38.

Cooperating with the cannula hub assembly 2 is the stylet hub assembly 6 having a proximal end 40, a hub 42 having a distal shoulder portion 44, and a distal stem portion 46 extending distally from the shoulder portion 44 and terminating at a distal end 48 which is fixedly attached to a proximal end of the sampling stylet 8. The external surface of the stylet hub 42 may, similar to the cannula hub 10, comprise a number of different designs. For example, as shown at FIGS. 1A and 1B, the proximal end 40 of the stylet hub assembly can include a thrust handle 52, the hub 42 may be ribbed with stylet hub rib extensions 53, 54, and 55, and the shoulder portion 44 may terminate at its proximal end into shoulder flange 56.

The distal end 48 of the stylet hub assembly is fixedly attached to the stylet 8 and further includes the pair of opposing flexible latching flanges 27 and 29, and a tip member 62. The flexible latching flanges 27, 29, removably latch the stylet hub distal end 48 within the cannula hub assembly 2 such as to orientate the stylet hub 42 in a spaced relationship to the canula hub 10. As shown in FIG. 1B, the tip member 62 is integral with the distal end 48 and cooperates with walls defining the longitudinal bore or cavity 15 in the cannula hub 10 and barrel member 14 which are dimensioned to allow a stylet distal end 66 and the tip member 62 to be slidably received into the cavity only when the tip member 62 is oriented such that the sampling stylet 8 and the cannula 4 sharpened distal ends 66 and 64, respectively, are oppositely directed and to deny access when the tip member 62 is otherwise orientated.

Figure 1B:
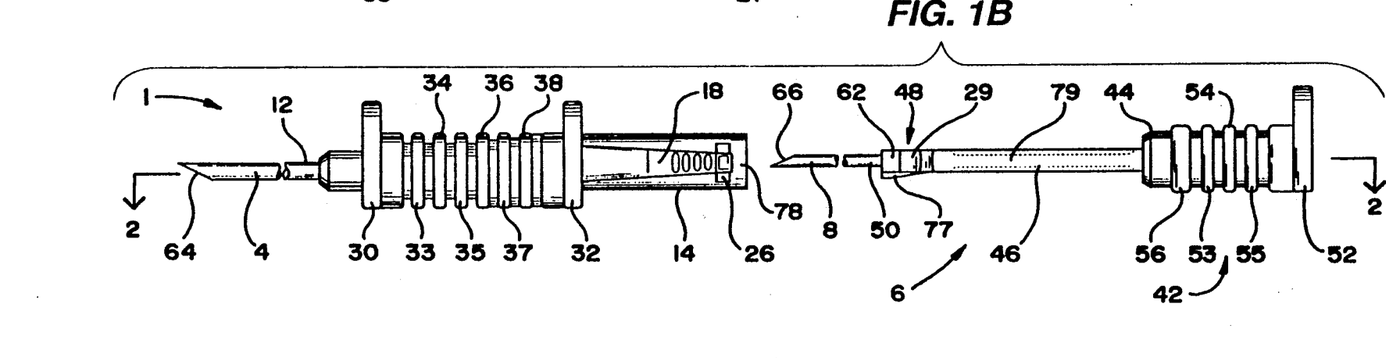
FIG. 1B is a longitudinal side plan view of the needle assembly shown in FIG. 1A.
Figure 2:
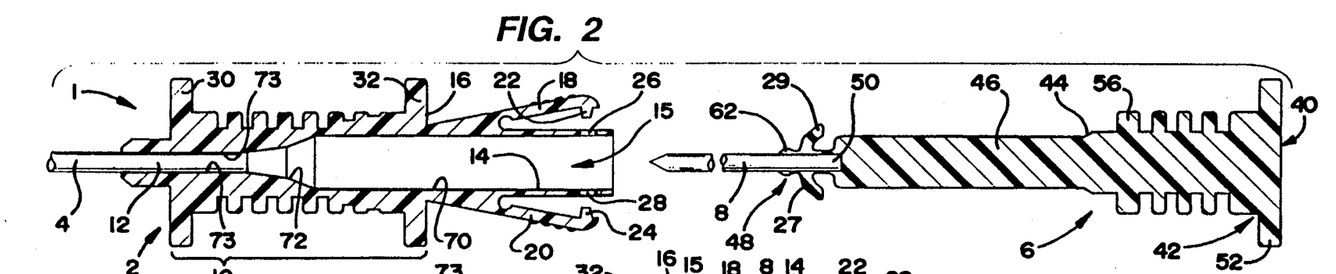
FIG. 2 is a longitudinal cross-sectional view through the needle assembly shown in FIG. 1A and is taken along line 2—2 of FIG. 1B.

FIG. 2 is a longitudinal cross sectional view through the needle assembly 1 and is taken along line 2—2 of FIG. 1B. As shown the longitudinal cavity or bore 15 includes a proximal straight bore 70 and a distal tapered or conical bore 72 axially aligned with and extending through barrel member 14 and a proximal portion of the cannula hub 10 to a small bore 73 receiving a proximal end 12 of the cannula 4.

The cooperative relationship between the longitudinal bore or cavity 15 and the tip member 62 may be further understood by reference to FIG. 3 and FIGS. 4A and 4B of the drawings. FIG. 3 is a cross-sectional view of the barrel member 14 of the cannula hub assembly 2 and shows that an otherwise circular contour of the longitudinal cavity 15 is interrupted by a planar limiting surface 74.

FIG. 4A is a front view of the tip member 62 of the stylet hub assembly distal end 48 only and shows the latching flanges 27 and 29, the tip member 62 and a boss 77 on one side of the tip member 62.

FIG. 4B is a transverse sectional view of the distal stem portion 46 of the stylet hub 42 and shows the stem portion 46 having opposite rounded side surfaces 79, 81 and opposite flat side surfaces 83, 85, each having spaced apart longitudinal grooves 89. The distal end 48 and the integral tip member 62, as well as the distal stem portion 46, of the stylet hub assembly 6 are slidably received into the longitudinal cavity or bore 15 only when the boss 77 is disposed adjacent a cylindrical wall surface 76 opposite the planar wall surface 74 in the longitudinal cavity 68. Similarly, planar surface 74 will be adjacent the flat surface 83. If the boss 77 is mistakenly inverted from the position illustrated at FIG. 4B in an attempt to install the same along the planar wall surface 74 of the longitudinal bore or cavity 15, wall body 78 outwardly of the planar wall surface 74 interferes to prevent receipt of the stylet hub assembly distal end 48 by contact with boss 77.

Figures 5A, 5B:
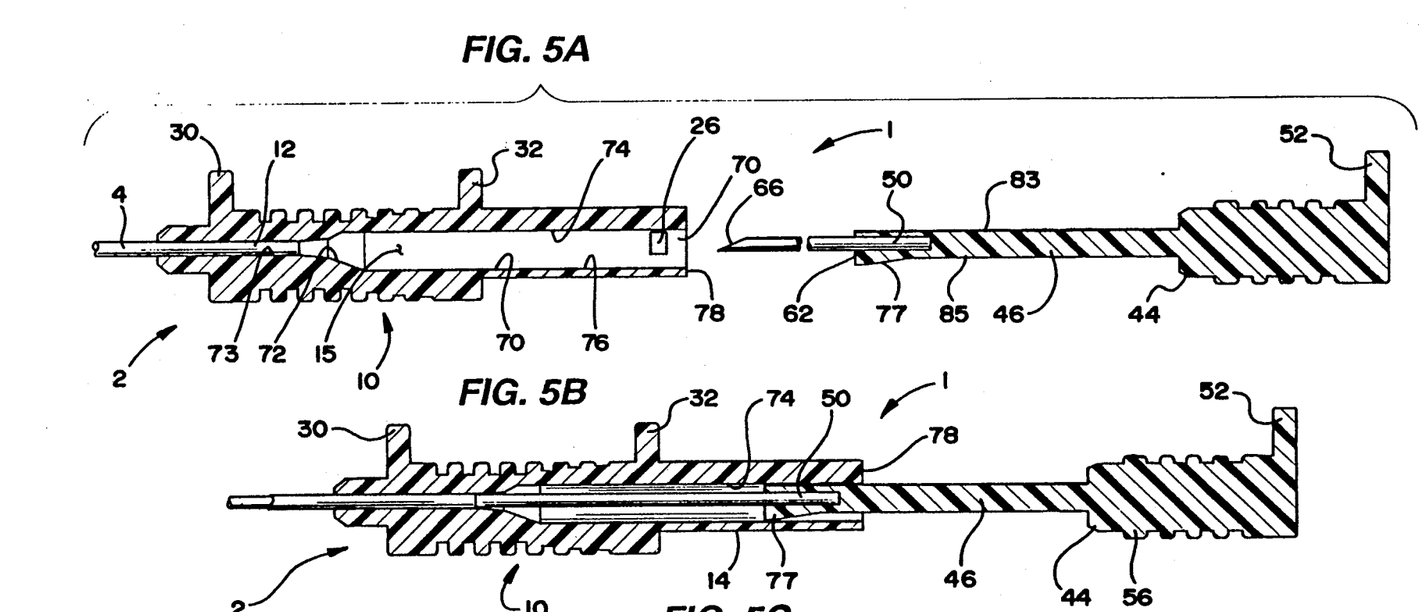
FIG. 5A is a longitudinal cross-sectional view of the needle assembly shown in FIG. 1B and is taken along line 5—5 of FIG. 1B and shows the stylet hub assembly separated from the cannula hub assembly.
FIG. 5B is a longitudinal cross-sectional view of the needle assembly, similar to the view shown in FIG. 5A, but showing the stylet hub assembly partially inserted into the cannula hub assembly.

FIG. 5A is a longitudinal vertical cross-section view of the needle assembly 1 taken along line 5—5 of FIG. 1A and shows the stylet hub assembly 6 separated from the cannula hub assembly 2.

Figure 5C:
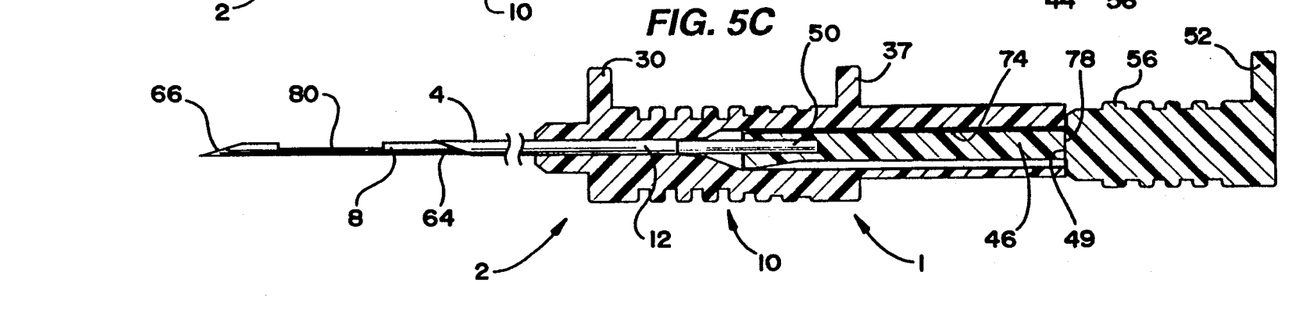
FIG. 5C is a longitudinal cross-sectional view of the needle assembly, similar to the view shown in FIG. 5A, but showing the stylet hub assembly fully inserted into the cannula hub assembly.

FIG. 5B shows the stylet hub assembly 6 partially inserted into the cannula hub assembly 2 and FIG. 5C shows the stylet hub assembly 6 fully inserted into the cannula hub assembly 6.

The tip member 62 and the stylet hub distal end 48, as well as the distal stem portion 46, may be slidably received into the longitudinal bore or cavity 15 only when the boss 77 is positioned adjacent cylindrical wall surface 76 of the longitudinal cavity 15 as shown in FIG. 5B. When fully inserted, as in FIG. 5C, the boss 77 will reach the distal tapered inner wall 72.

The adjacent flat planar surfaces, surface 83 on stem portion 76 and surface 74 in longitudinal cavity 15, prevent undesirable rotational movement of the stylet 8 relative to the cannula 4. At this position, a proximal end 78 of barrel member 14 abuts against shoulder portion 44 of the stylet hub assembly 6 and the sharpened distal ends 64 and 66 of the cannula 4 and of the sampling stylet 8 are oppositely directed.

Figures 6, 7A, 7B:
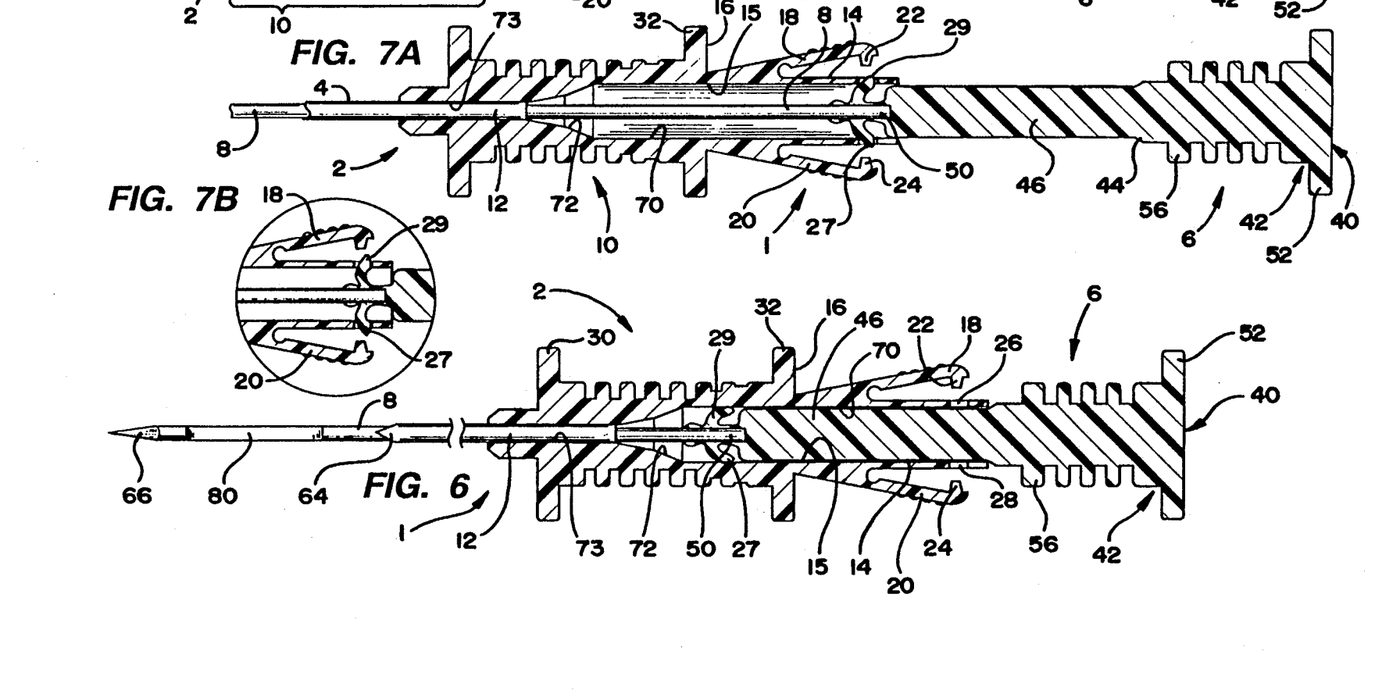
FIG. 6 is a longitudinal cross-sectional view through the needle assembly shown in FIG. 2, similar to the view shown in FIG. 2, but showing the stem portion of the stylet hub assembly fully inserted into the cannula hub assembly.
FIG. 7A is a longitudinal cross-sectional view through the needle assembly, similar to the view in FIG. 6, but showing the stem portion of the stylet hub assembly retracted proximally within the cannula hub assembly to a position where a pair of flexible latching flanges opposite each other on the stylet hug distal end have flexed radially outwardly into a corresponding pair of cut out slots in a barrel member of the cannula hub assembly thereby to orientate the stylet hub assembly in a spaced relationship to the cannula hub.
FIG. 7B is a cross-sectional view of the flexing latching flanges when the cannula is pushed forward to cover the stylet to collect a biopsy sample and shows the flexed position of the latching flanges axially rearwardly and radially outwardly.

There is illustrated in FIG. 6 a longitudinal cross-sectional view through the needle assembly 1, similar to the view in FIG. 2, showing the stem portion 46 of the stylet hub assembly 6 fully inserted into the cannula hub assembly 2. When the needle assembly 1 is in this fully inserted position, the pair of flexible latching flanges 27 and 29 are radially inwardly flexed and abut against the walls of the bore 70 of the barrel member 14 in the longitudinal cavity 15.

FIG. 5C also illustrates the assembled needle assembly 1 which includes the cannula 4 extending distally from the cannula hub assembly 2 and shows the sharpened distal end 64 of the cannula 4 facing downwardly and the sharpened distal end 66 of the sampling stylet 8 facing upwardly, and an adjacent upwardly facing biopsy sample/specimen receiving notch 80 ground into the stylet 8 just behind the stylet sharpened distal end 66. The stylet 8 is telescopically disposed within the cannula 42 and is extendable from the distal end 64 of the cannula 2. It is preferable that the cannula 2 and the sampling stylet 8 of the needle assembly 1 have sharpened distal ends 64, 66 oppositely directed and that this relationship be maintained as such orientation is necessary for effective biopsy collection.

FIG. 7A is a longitudinal cross-sectional view of the needle assembly 1, similar to the view shown in FIG. 6 but showing the stem portion 46 of the stylet hub assembly 6 retracted proximally from the cannula hub assembly 2 where the pair of flexible latching fingers 27, 29 snap into the corresponding pair of cutoff slots 26, 28 in the barrel member 14 of the cannula hub assembly 2 thereby to orientate the stylet hub 42 in a spaced relationship to the cannula hub 16. When the stylet hub assembly 6 is retracted proximally from the fully inserted position illustrated in FIG. 6, the pair of flexible latching flanges 27 and 29 remain radially inwardly flexed and brush against the wall of the bore 70 until the latching flanges 27, 29 flex outwardly into the pair of opposite cutout slots 26 and 28 in the barrel member 14. The stylet hub assembly distal end 48 is then removably latched within the barrel member 14 of the cannula hub assembly 2 such as to orientate the stylet hub assembly 6 in a spaced relationship to the cannula hub assembly 2. This spaced relationship may be defined to match the exact position necessary to properly load the oriented biopsy needle assembly 1 into a tissue sampling device of the type disclosed in U.S. Pat. No. 4,699,154. At this position, the pair of flexible latching flanges 27 and 29 received in the slots 26 and 28 are axially aligned with the extending detents 22 and 24 of the pair of inwardly flexible finger pinching arms 18 and 20 so that a pinching of the flexible finger pinching arms 18, 20 will cause the detents 22 and 24 to co-act with and inwardly move or flex the pair of flexible latching flanges 27 and 29 allowing the stylet hub assembly distal end 48 to be proximally removed from the cannula hub assembly 2 by continued retraction of the stylet hub assembly distal end 48, 62 from the barrel member 14. Such proximal removal of the sampling stylet 8 allows examination of the biopsy collection to ensure adequacy of the sample size, or to determine that the sample is from the correct location, or to obtain multiple collections without removal of the cannula 4 from the biopsy site.

FIG. 7B is a cross sectional focal view of the flexible latching flanges 27 and 29, similar to FIG. 7A, but illustrating the flexible latching flanges 27 and 29 being both outwardly and radially extended and backwardly and axially extended when the cannula 4 is pushed forward to cover the specimen notch 80 to collect the biopsy sample, such as by an actuating device and there is overshoot or overtravel of the cannula hub assembly 2 relative to the stylet hub assembly 6, the latching flanges 27, 29 absorb the stress of the overtravel and flex as shown. Stated otherwise, the flanges are constructed and designed to flex inwardly, outwardly, and backwardly flexible in both a radial and axial manner relative to the needle assembly 1, thereby to cushion or resist the driving force of the cannula 4 over the stylet 8 during the cannula collecting stroke for collecting the biopsy sample. During the cannula collecting stroke, particularly in automatic devices such as the tissue sampling device of U.S. Pat. No. 4,699,154, the cannula 4 momentarily overtravels or overextends the stylet distal end 66 entrapping a sheared tissue specimen within the specimen notch 80 before returning to its final position at the completion of the collection stroke. Thus it is advantageous that the latching flanges 27, 29 be bidirectionally flexible in an axial and radial manner relative to the needle assembly 1 to avoid being sheared off or broken and to serve as a shock absorber for the cannula hub assembly 2 during the cannula collection stroke.

Figure 8A:
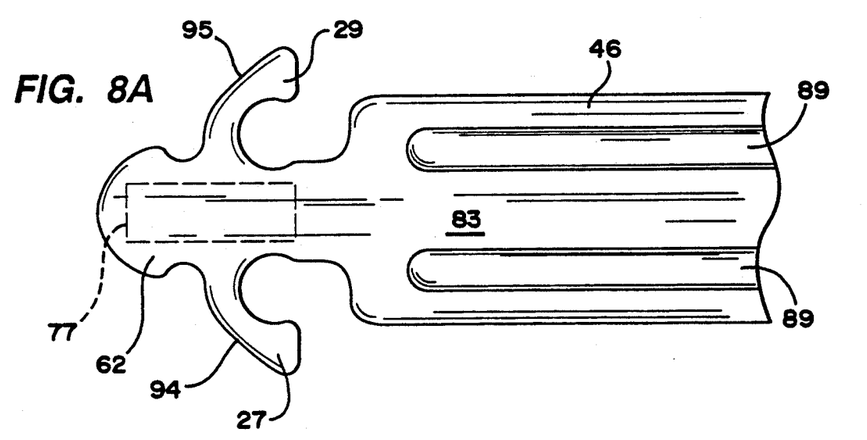
FIG. 8A is an enlarged top plan view of the distal end of the stylet hub assembly showing the latching flanges

FIG. 8A is an enlarged plan view of the stylet hub assembly distal end 48 and shows the latching flanges 27 and 29. Note that each latching flange 27, 29 has a rearwardly curved or rearwardly inclined surface 94, 95 which facilitates a smooth easy movement of the flanges 27, 29 and the whole stylet hub assembly 6 forwardly in the longitudinal bore 15 upon actuation of an associated tissue sampling device.

Figure 8B:
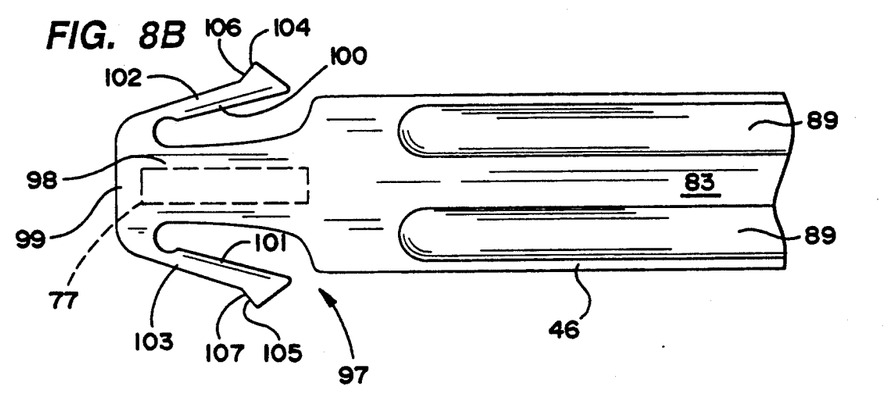
FIG. 8B is an enlarged top plan view of the distal end of a modified stylet hub assembly showing a different type of latching flange.

FIG. 8B illustrates an alternative embodiment of a stylet hub assembly distal end 97 which is generally M-shaped when viewing the same as shown in FIG. 8B. The stylet hub assembly distal end 97 includes a distal end body 98 terminating at a distal head 99 which is integral with a pair of rearwardly and radially outwardly extending flexible latching flanges 100 and 101, each having a rearwardly inclined surface 102 and 103 ending in a triangularly shaped detent 104 or 105.

The flange outer surfaces 102 and 103, respectively, and an inclined surface 106 or 107 of one of the detents 104 or 105 facilitate smooth forward movement stylet hub assembly distal end 97 in the longitudinal bore 15.

Figure 8C:
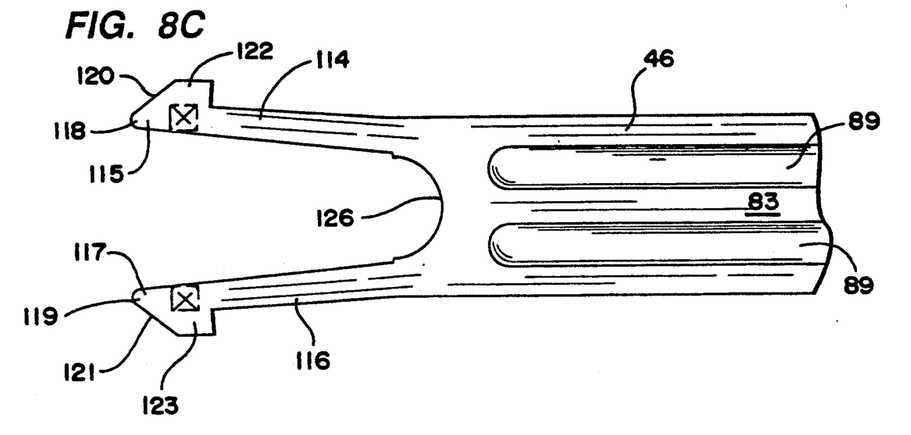
FIG. 8C is an enlarged top plan view of the distal end of another modified stylet hub assembly showing still another type of latching flange.

FIG. 8C shows another embodiment of a stylet hub assembly distal end 110 which is generally U-shaped when viewed as shown in FIG. 8C. In this embodiment, a pair of flexible latching flanges 114 and 116 are aligned opposite each other and terminate in a blocked shaped detent 115 or 117. Each detent 115, 117 has a distal detent end 118 and 119 integral with an outwardly rearwardly inclined external surface 120 or 121 which terminate in a blocked shaped boss 122 or 123. The flanges 114 and 116 are integral with the stylet hub assembly distal stem portion 46 and are separated by a curved surface 126 which defines the bight of the U.

The present invention provides an oriented biopsy instrument or needle assembly 1 which is disposable. The relatively simple two piece construction of a cannula hub assembly 2 and a stylet hub assembly 6 may be made at minimal cost using plastic resins suitable for injection molding. The cannula 4 and stylet 8, of course, are made of stainless steel.

It is believed that the oriented biopsy needle assembly 1 of the present invention in its described embodiment and with advantages described above and inherent therein will be fully understood from the foregoing description, and that changes may be made in form, construction, and arrangement of the several parts thereof without departing from the teachings of the invention or sacrificing any of the advantages therein. The preferred embodiments illustrated are not intended to be exhaustive or to limit the invention to the precise form disclosed. Accordingly, the scope of the invention is only to be limited as necessitated by the accompanying claims.

We claim:

1. An oriented biopsy needle assembly comprising:
    a cannula hub assembly including a cannula hub having a proximal end and a distal end and a cannula extending distally from said cannula hub and having a sharpened distal end;
    a sampling stylet having a proximal end, a sharpened distal end and a biopsy sample receiving notch adjacent the distal end and being telescopically received within said cannula and extendable from said distal end of said cannula;
    said cannula hub assembly further including a barrel member fixed to said proximal end of said cannula hub, said barrel member and said cannula hub having a longitudinal coaxial bore therethrough axially aligned with and extending to said cannula;
    a stylet hub assembly having a proximal end, a stylet hub at said proximal end, a shoulder portion at a distal end of said hub, and a stem portion extending distally from said shoulder portion and terminating at a distal end which is fixedly attached to a proximal end of said sampling stylet, said stem portion fitting non-rotatably into the longitudinal opening in the cannula hub assembly and being longitudinally slidable therein between retracted and extended positions, the distal end of the stylet being extended forwardly from the distal end of the cannula such that the biopsy sample receiving notch is exposed when the stem portion is in its extended position, the stem portion and longitudinal opening being shaped such that the stem portion is constrained to fit into the longitudinal opening at a particular angular orientation with respect to the longitudinal opening, such that the sharpened distal ends of the cannula and sampling stylet are oppositely directed;
    latching means on said cannula hub assembly and said stylet hub assembly for releasably retaining said stem portion in its retracted position within the longitudinal opening in said cannula hub assembly, the latching means comprising a pair of cutout slots at a proximal end of the barrel member which extend through the wall of said barrel member and into the longitudinal opening therein and which are aligned laterally opposite each other, said stylet hub assembly having a pair of laterally opposed, radially extending flexible latching flanges on the distal end of the stem portion, said slots and said flanges being constructed and arranged to mate with each other at the retracted position of the stem portion where the flanges snap into said slots, each flexible flange having a forward facing surface that is curved or inclined in an outward and rearward direction such that the flanges are resiliently deflected radially inwardly when the stem portion is moved longitudinally forwardly from its retracted to its extended position, thus facilitating movement of the stem portion in such forward direction, the flanges resiliently flexing in a forward direction when the stem is urged longitudinally in a rearward direction relative to the barrel member from its retracted position, thus restraining the stem from moving rearwardly past its retracted position but permitting at least limited resilient overtravel of the stem rearwardly in the retracted position; and
    manually actuatable unlatching means for releasing the latching means so as to permit withdrawal of the sampling stylet from the cannula without removing the cannula from a patient.

2. The oriented biopsy needle of claim 1 wherein said unlatching means comprise laterally oppositely disposed, inwardly flexible finger pinching arms which extend outwardly from the outer surface of said barrel member, each arm having an inwardly extending detent positioned for movement into one of said slots to engage one of said flexible latching flanges to move it inwardly to unlatch each latching flange from one of said slots when said finger pinching arms are flexed inwardly.

3. The oriented biopsy needle assembly according to claim 1 wherein the stylet hub assembly includes a tip member at said distal end of said stem portion having a boss on one side thereof, said stem portion having a flat surface on a side opposite said boss, said longitudinal bore in said barrel member having a cylindrical wall surface and a flat wall surface, and said tip member being slidably received into said bore when said tip member is oriented such that said cannula and sampling stylet sharpened distal ends are oppositely directed and said boss is then located adjacent said cylindrical wall surface and said flat surface of said stem portion is then located adjacent said first wall surface in said bore.

4. The oriented biopsy needle assembly according to claim 1 wherein an external surface of the cannula hub is at least partially ribbed.

5. The oriented biopsy needle assembly according to claim 1 wherein an external surface of the stylet hub is at least partially ribbed.

6. An oriented biopsy needle assembly according to claim 1 wherein the flanges extend radially outwardly and rearwardly from the stem and include tips on distal ends that fit in the slots to resiliently resist movement the stem out of the retracted position in both a forward and a rearward direction, the flanges and tips being formed such that forward stem movement causes the tips to deflect inwardly out of the slots so as to permit forward stem travel to the extended position, whereas rearward movement of the stem urges the flanges to pivot forwardly and to extend further into the slots so as to provide a cushioned stop for the stem when it travels from the extended to its retracted position with respect to the longitudinal opening.

* * * * *